United States Patent [19]

Shields

[11] 4,312,999

[45] Jan. 26, 1982

[54] GLYOXAL-POLYAMINE REACTION PRODUCTS AND PROCESS FOR THEIR PREPARATION

[75] Inventor: Theodore C. Shields, Ashland, Ky.

[73] Assignee: Ashland Oil, Inc., Ashland, Ky.

[21] Appl. No.: 124,817

[22] Filed: Feb. 26, 1980

Related U.S. Application Data

[63] Continuation-in-part of Ser. No. 2,171, Jan. 9, 1979, Pat. No. 4,247,404.

[51] Int. Cl.$^3$ .................. C07C 119/08; C07C 119/12
[52] U.S. Cl. .................................. 564/279; 210/698; 252/82; 252/180; 528/245
[58] Field of Search .................. 564/278, 279; 252/82, 252/180; 528/245

[56] References Cited

U.S. PATENT DOCUMENTS

| | | | |
|---|---|---|---|
| 2,849,486 | 8/1958 | Tousignant | 564/278 |
| 3,372,086 | 3/1968 | Westfall et al. | 528/245 |
| 3,475,359 | 10/1969 | Cummings | 528/245 |
| 3,506,613 | 4/1970 | Bayer | 528/245 |

*Primary Examiner*—Natalie Trousof
*Assistant Examiner*—L. Hendriksen
*Attorney, Agent, or Firm*—Sughrue, Mion, Zinn, Macpeak & Seas

[57] ABSTRACT

Oxalyl compounds and polyalkylene polyamine derivatives of ethylene diamine and higher homolog polyamines are reacted to form a reaction product. This product is useful as an antifouling agent in the water systems of boiler and scrubbers, and particularly the quenching waters of blast furnaces.

16 Claims, No Drawings

GLYOXAL-POLYAMINE REACTION PRODUCTS AND PROCESS FOR THEIR PREPARATION

This application is a continuation-in-part of Ser. No. 2,171, filed Jan. 9, 1979, now U.S. Pat. No. 4,247,404, which is hereby incorporated by reference.

This invention relates to novel water-soluble compositions, and a process for their preparation. More particularly, the invention is concerned with water-soluble compositions produced by reacting oxalyl compounds with ethylene and higher homolog polyamines to produce a reaction product.

One object of this invention is to provide compositions which are adapted for use as antifouling agents in boiler waters and in other industrial water systems.

Another object of this invention is to provide a composition which can be reacted further with polybutenyl succinic anhydride to make a reaction product useful as an additive in lubricating oil formulations.

SUMMARY OF THE INVENTION

Briefly stated, this invention comprises in one aspect a process for preparing the reaction product of this invention comprising the steps of:

Reacting an alkylamino substituted ethylene diamine or homologous polyamine of the general formula:

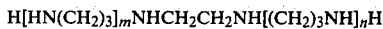

where m+n is between 2 and 6 with an oxalyl compound or mixture of oxalyl compounds of the structural formula:

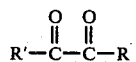

where R and R' are each either hydrogen or an alkyl radical of 1 to 4 carbon atoms.

The resultant product is an effective antifouling agent for boiler waters and scrubber waters for blast furnaces. The resultant product is also useful as an intermediate product which subsequently can be reacted with polybutenyl succinic anhydride to make a product useful in lubricating oil formulations.

In another aspect, this invention comprises the reaction product obtained by the above-described process.

DETAILED DESCRIPTION OF THE INVENTION

The oxalyl compound used in the making of the dispersant of this invention is one having the structural formula:

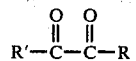

where R is either hydrogen on an alkyl radical of 1 to 4 carbon atoms and R' is either hydrogen or an alkyl radical of 1 to 4 carbon atoms. Preferably R' and R are hydrogen so that the most preferable oxalyl compound is glyoxal which has the structural formula:

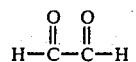

In water solution glyoxal is believed to be a mixture of a series of hydrated forms. Commercially, glyoxal is supplied as a light-yellow aqueous solution containing a minimum of 30% by weight of glyoxal, and small amounts of ethylene glycol, glycolic acid, formic acid, and formaldehyde.

Other glyoxal compounds which can be used include pyruvic aldehyde ($CH_3COCHO$) and 2,3-butanedione.

Preferred alkylamino derivatives of ethylene diamine are:

(a) 4,7-diazadecane-1,10-diamine
(b) 4,7,11-triazatetradecane-1,14-diamine
(c) 4,8,11,15-tretraazaoctadecane-1,18-diamine
(d) a mixture of 60% to 40% of 4,7,11-triazatetradecane-1,14-diamine and 40% to 60% 4,8,11,15-tetraazaoctadecane-1,18-diamine.
(e) other mixtures of the above-named polyamines; and
(f) mixtures of one or more of the above-named amines also containing up to 50% by weight of 3-azahexane-1,6-diamine.

Of these amines the 4,7-diazadecane-1,10-diamine and a mixture of 60% of 4,7,11-triazatetradecane-1,14-diamine and 40% 4,8,11,15-tetraazaoctadecane-1,18-diamine are most preferred.

Throughout the remainder of the specification glyoxal will be specified as the oxalyl compound. It is not to be inferred however, that the other oxalyl compounds previously mentioned could not also be used.

In the preparation of the composition of this invention, the glyoxal and the polyamine are mixed together preferably in a mole ratio of 1 mole of glyoxal to 2 moles of polyamine. An excess of either reactant can be used but is not particularly desirable.

If desired, this reaction step can be conducted in the presence of substantially inert organic liquid diluents. The presence of the diluent can facilitate temperature control and the mixing of the reactants. If a diluent is selected which will form an azeotrope with water, the diluent assists in the removal of water. Suitable diluents include, for example, the normally aliphatic, cycloaliphatic, and aromatic hydrocarbons and the corresponding halogenated hydrocarbons, particularly chlorinated hydrocarbons, such as benzene, toluene, xylene, chlorobenzene, hexane, heptane, cyclohexane, mineral oil, mixtures thereof, and the like. Water may also be used as the inert liquid diluent in the step. However, for commercial practicability it is preferred to add only a minimum amount of water.

The reaction between the glyoxal and the amine is exothermic and the temperature is maintained between −30° C. and 120° C. or preferably between 0° C. and 60° C. until the evolution of heat subsides. The mixture is then refluxed for a period of time sufficient to insure reaction, preferably at a temperature of around 50° C., and is then subjected to stripping preferably at a reduced pressure and a maximum temperature of 200° C. to remove water of reaction and/or carrier liquid. The resulting product is the desired product.

Generally, the water-soluble compositions of this invention can be used in water systems alone or in combination with other conventionl additives. When employed in a blow-down water system in a steel mill, for example, the compositions can be used in concentrations of between 50 and 5000 parts per million. A preferred concentration is 500 to 1500 ppm.

The water-soluble compositions of this invention can be effectively employed in a variety of water systems. A particular water system is the so-called "blow-down"

system used in steel mills. In such a system water is sprayed on the hot gases emerging from the steel-making process. These gases contain concentrations of acidic gases such as the oxides of nitrogen and sulfur. The resulting aqueous solution of these gases is highly corrosive so that an antifouling agent such as that of this invention must be added to prevent corrosion and fouling of the equipment.

The compositions of this invention are also useful as the intermediate product in the formulation of the dispersant compounds disclosed in my appending application, Ser. No. 2,171, filed Jan. 9, 1979.

The following examples illustrate preferred embodiments of the process for preparing the water-soluble compositions of this invention and the resultant compositions.

EXAMPLES

Compositions were prepared by reacting glyoxal and the following amine materials:
A. 4,7-diazadecane-1,10-diamine
B. 60% 4,7,11-triazatetradecane-1,14-diamine and 40% 4,8,11,15-tetrazaoctadecane-1,18-diamine
C. 40% 4,7,11-triazatetradecane-1,14-diamine and 60% 4,8,11,15-tetrazaoctadecane-1,18-diamine using a 40% aqueous solution of glyoxal in the proportions as follows and added water:

|  | Run No. | | |
| --- | --- | --- | --- |
|  | 2-66 | 3-9 | 3-7 |
| Amine | A | B | C |
| Amine grams (moles) | 174(1.0) | 100.3(0.4) | 104.8(0.4) |
| Distilled Water ml. | 300 | 200 | 200 |
| 40% Glyoxal Solution grams (moles) | 72.5(0.5) | 29.0(0.2) | 29.0(0.2) |
| Product, grams | 185.1 | 104.6 | 113.2 |

In each run the amine was charged to a one-liter stirred flask. Distilled water, 1.7 to 2.0 grams water per gram of amine, was added and the solution cooled to 0° C. The 40% glyoxal aqueous solution was then added with the reaction temperature maintained between 0° C. and 2° C. The mixture was heated to reflux (approximately 100° C.) over a 30 minute period. Water was distilled overhead at a 60° C. maximum temperature under a vacuum of 75–100 mm of mercury. Isopropanol was then added to aid in the removal of residual water and the solvents again removed under vacuum at a maximum temperature of 120° C. The resulting products were the desired reaction products.

The effectiveness of the compositions of this invention are demonstrated by the following tests which is a modification of ASTM Method G-31-72. Tap water was boiled down to 10% of its original volume to concentrate scale-forming impurities therein. Concentrations of the reaction product obtained from reacting C above with the 40% glyoxal solution were added to the water in the concentration shown below in runs X, Y and Z. Run W was a control run. Mild steel coupons were then immersed half way into each of the solutions after the solution had been sparged with nitrogen gas. Each sample was then closed under a nitrogen atmosphere and held at 100° C. for 90 days. The amount of scale built upon each sample was then determined. Results are shown below.

| RUN NUMBER | CONCENTRATION IN CONDENSED TAP WATER | SCALE BUILDUP, MILLIGRAMS |
| --- | --- | --- |
| W | 0 | 31.8 |
| X | 1000 ppm | 19.2 |
| Y | 600 ppm | 25.2 |
| Z | 200 ppm | 35.3 |

From these tests it is readily apparent that a concentration of between 1000 and 500 ppm resulted in substantial reduction of scaling.

I claim:

1. A process for preparing water-soluble compositions comprising reacting an alkylamino substituted ethylene diamine or a homolog thereof having the structural formula:

with an oxalyl compound or mixture of oxalyl compounds of the structural formula:

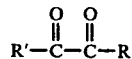

where R and R' are each hydrogen or an alkyl radical of 1 to 4 carbon atoms and m+n is between 2 and 6, thereby obtaining said product, the mole ratio of diamine or homolog thereof to oxalyl compound being about 2 to 1, said product being water-soluble.

2. The process of claim 1 wherein said diamine is selected from the group consisting of 4,7-diazadecane-1,10-diamine, 4,7,11-triazatetradecane-1,14-diamine, 4,8,11,15-tetraazaoctadecane-1,18-diamine, mixtures thereof, and mixtures thereof containing 3-azahexane-1,6-diamine.

3. The process of claim 1 wherein said diamine is 4,7-diazadecane-1,10-diamine.

4. The process of claim 1 wherein said diamine is 4,7,11-triazatetradecane-1,14-diamine.

5. The process of claim 1 wherein said diamine is 4,8,11,15-tetraazaoctadecane-1,18-diamine.

6. The process of claim 1 wherein said diamine is a mixture of 60% to 40% of 4,7,11-triazatetradecane-1,14-dimaine and 40% to 60% 4,8,11,15-tetraazaoctadecane-1,18-diamine.

7. The process of claim 1 wherein said diamine contains up to 50% by weight of 3-azahexane-1,6-diamine.

8. The process of claim 1 wherein said oxalyl compound is glyoxal.

9. The process of claim 1 wherein said oxalyl compound is pyruvic aldehyde.

10. The process of claim 1 wherein said oxalyl compound is 2,3-butanedione.

11. The process of claim 1 wherein said polyamine is 4,7-diazadecane-1,10-diamine and said oxalyl compound is glyoxal.

12. The process of claim 1 wherein said diamine is a mixture of between about 40% and 60% by weight of 4,8,11,15-tetraazaoctadecane-1,18-diamine and 60% to 40% by weight of 4,7,11-triazatetradecane-1,14-diamine.

13. The process of claim 1 wherein the reaction is conducted at a temperature between about 0° C. and about 50° C.

14. The product produced by the process of one of claims 1–13.

15. The process of one of claims 1, 8, 9, 10 or 13 wherein each of m and n is at least 1.

16. The product of claim 14 wherein each of m and n is at least 1.

* * * * *